United States Patent [19]

Orsolini et al.

[11] Patent Number: 4,673,595
[45] Date of Patent: Jun. 16, 1987

[54] MICROENCAPSULATION BY PHASE SEPARATION OF WATER-SOLUBLE MEDICAMENTS

[75] Inventors: Piero Orsolini, Martigny; Rolland-Yves Mauvernay; Romano Deghenghi, both of Lausanne, all of Switzerland

[73] Assignee: Debiopharm, S.A., Switzerland

[21] Appl. No.: 787,249

[22] Filed: Oct. 15, 1985

[30] Foreign Application Priority Data

Oct. 17, 1984 [CH] Switzerland ................. 4979/84

[51] Int. Cl.[4] ................. A61K 9/36; A61K 9/52; B01J 13/02
[52] U.S. Cl. ................. 427/213.32; 264/4.3; 424/450; 424/497; 428/402.24
[58] Field of Search ................. 264/4.3; 427/213.32; 424/35, 19; 428/402.24

[56] References Cited

U.S. PATENT DOCUMENTS 3,173,878  3/1965  Reyes ................. 264/4.6
4,166,800  9/1979  Fong ................. 428/402.24 X

FOREIGN PATENT DOCUMENTS 0052510  5/1982  European Pat. Off. ............. 424/19

*Primary Examiner*—Richard D. Lovering
*Attorney, Agent, or Firm*—Omri M. Behr

[57] ABSTRACT

The microencapsulation of medicamentous water-soluble substances is carried out by phase separation. The operations of the hardening step take place at a temperature comprised between about 0° and about 25° C., the non-solvent used during this step being an aliphatic fluorinated or fluorohalogenated hydrocarbon or a mixture of such hydrocarbons. Further, the non-solvent is used in an excess with respect to the volume of solvent and non-solvent resulting from the phase-separation step.

10 Claims, No Drawings

MICROENCAPSULATION BY PHASE SEPARATION OF WATER-SOLUBLE MEDICAMENTS

BACKGROUND OF THE INVENTION

The microencapsulation of medicamentous substances is an established technique, which in particular permits the protection and the controlled administration of medicamentous substances having a short half-life in vivo. The resulting galenic form most often has the form of an injectable suspension of a very high efficiency.

Various methods of realization are described in the literature (see for example the patent Application EP No. 0052510). One of the most used methods of microencapsulation by phase separation can be described as follows:

(a) a biocompatible polymer is first dissolved in an organic solvent non-miscible with water (for example $CH_2Cl_2$);

(b) an aqueous solution of the selected medicamentous substance is then dispersed in the above-mentioned organic solution;

(c) a said non-compatible polymer, such as a silicone oil, is then introduced under stirring into the dispersion obtained as described in (b) causing embrionic microcapsules to form by the deposition of the polymer initially dissolved on the dispersed medicamentous substance;

(d) the mixture obtained in (c) is then poured into an excess of an organic solvent non-miscible with water and non-solvent for the deposited polymer, such as for example heptane, thus causing the hardening of the microcapsules through the extraction of the initial organic solvent (for example $CH_2Cl_2$) still contained in the mass of the deposited polymer;

(e) the microcapsules thus hardened are then filtered, washed and dried, or even sterilized according to usual techniques.

The analyses which were carried out showed that the microcapsules dried to constant weight, still contained a high portion in weight of undesirable organic compounds, such as the heptane used during the step (d) hereabove. In a number of cases, the quantity of residual organic solvent turned out to be in fact equivalent or even higher, than that of the microencapsulated active principle (medicamentous substance), which strongly compromised any pharmaceutical application of such preparations.

Independently from the foregoing, it was found that aggregates of microcapsules were often obtained in the step of the phase separation, as well as during the hardening of the microcapsules, which results in important decreases in the yield, or even in the refusal of certain batches, which thus had become unusable.

According to the U.S. patent No. 4 166 800, the occurrence of such a phenomenon can be prevented by operating at temperatures comprised between $-100°$ and $-40°$ C. during the step of the phase separation, as well as during the hardening by the addition of a non-solvent of the polymer. Heptane is indicated as a choice non-solvent for the hardening.

To conduct industrially operations at such low temperatures is expensive and is a source of complications. Further, the use of organic solvents, such as for example heptane on an industrial scale presents a major drawback, i.e. the emission of large amounts of inflammable or even toxic vapours.

PREFERRED EMBODIMENTS OF THE INVENTION

The difficulties set forth in the foregoing can be advantageously solved by the present invention. In fact, it was unexpectedly found that by operating at a temperature comprised between about $0°$ and about $25°$ C. during the hardening of the microcapsules and by using as a non-solvent during the hardening step a fluorinated or a fluorohalogenated hydrocarbon or a mixture of such hydrocarbons in an excess with respect to the total volume of solvent and of non-solvent resulting from the step of the phase separation, any formation of aggregates was advantageously eliminated. It was further found that the microcapsules which were thus obtained contained only a very small residue of undesirable organic compounds, or at least a residue which was perfectly acceptable for the therapeutical administration of said microcapsules.

Further to the quality of being readily eliminated during the usual drying operations, said hydrocarbons further presented the advantage of being non-toxic and non-inflammable, and consequently adapted for use on an industrial scale.

Depending on the case, a reduction of the level of residual non solvent in the microcapsules obtained by the process of the invention from 10 to 1 or even less can be achieved.

The microcapsules obtained by the process of the invention are further considerably more stable than those obtained by the usual methods. In particular, it was observed that the coating layer of the polymer as significantly less prone to degradation, for example through hydrolysis, during ageing tests.

The word non-solvent in the foregoing serves in fact to designate a liquid organic compound non-miscible with water, and causing no dissolution of the polymer making up the essential mass of the microcapsules. When added to an aqueous organic suspension of embrionic microcapsules (step (c) in the foregoing) it causes the hardening of the latter by extracting the organic solvent initially contained in the mass of the polymer, for example $CH_2Cl_2$.

It was observed that the process of the present invention was suited for the microencapsulation of a considerable variety of medicamentous water-soluble substancs. As non-limiting examples of medicamentous substances, one can cite water-soluble polypeptides such as the release hormone of the luteinizing hormone and of the follicle stimulating hormone (LH—RH), or one of its synthetic analogs (on this subject, see Patent CH No. 615 662), somatostatin or one of its synthetic analogs, human or animal calcitonin, human or animal growth hormone, release hormone of the growth hormone, a cardiopeptide such as ANP (human 1–28) or an interferon, natural or recombined.

Generally, the medicamentous substances which can advantageously be microencapsulated by using the method of the invention can be chosen among substances having an anti-inflammatory, antitumorous, immunodepressive, antithrombotic, neuroleptic, antidepressive, or an antihypertensive effect, or among the non-toxic water-soluble salts of such substances.

As an example of a non-solvent in the sense of the present invention, one can advantageously use the fluorinated or the fluorohalogenated aliphatic hydrocarbons sold commercially, such as those sold under the trade name FREON. Said hydrocarbons will be preferably selected from those which are in a liquid form at atmospheric pressure, and at a temperature comprised between about 0° and about 25° C. Particularly interesting results were observed when trichlorofluoromethane, 1,1,2-trichlorotrifluoroethane, or 1,2-dichlorotetrafluoroethane were used. This enumeration is however not exhaustive.

According to the invention, said non-solvent is used in an excess with respect to the total volume of solvent and non-solvent resulting from the phase-separation step. It is preferable to use an excess of at least 5:1 or even 10:1, depending on the case. The formation of aggregates is thus advantageously avoided.

The method of the invention is successfully applied to the preparation of microcapsules based on a variety of biocompatible polymers. As examples of such polymers, one can cite the polymers of L-lactide, D,L-lactide or copolymers of D,L-lactide and glycolide.

The examples will illustrate the invention in a more detailed manner, without however limiting its scope.

EXAMPLE 1

Coating of a placebo by microencapsulation

A. 1.0 g of a copolymer of D,L-lactide and glycolide about 50:50 (average molecular weight 53,000) was first dissolved at 25° C. in 50 g of methylene chloride and placed in a reactor provided with a stirring turbine. Thereafter, 300 micro-l or water were added progressively to the organic mixture. During this addition, the stirring was maintained at about 2000 rpm. 30 ml of silicone oil (Dow Corning Fluid 200) were then introduced at 25° C. into the reaction medium under stirring at the rate of about 2 ml/min. Once the addition of silicone oil was terminated, the mixture containing the embrionic microcapsules was poured at 25° C. into 2 l of 1,1,2-trichloro-trifluoroethane to permit them to harden, and stirred for 30 minutes at about 800 rpm. After filtration, the resulting product was dried under reduced pressure for 24 h. The product thus obtained was isolated with a yield of 76% (of theoretical).

B. The above operations were repeated in practically identical conditions, the 1,1,2-trichlorotrifluoroethane being replaced by an identical amount of trichlorofluoromethane, and the hardening being carried out at 15° C.

C. As a comparison, the above operations were repeated, the non-solvent used during the hardening step being heptane.

Each of the samples thus prepared was then dried under vacuum over a prolonged period until constant weight was achieved. The results obtained are given below:

| Sample | Loss in weight | Residual solvent |
| --- | --- | --- |
| A | 3% | 5% (1,1,2-trichloro-trifluoroethane) |
| B | 15% | 0.5% (trichlorofluoromethane) |
| C | 5% | 8% (heptane) |

EXAMPLE 2

Coating of a decapeptide by microencapsulation

The microencapsulation operations conducting to the preparation of a pharmacologically active coated compound were carried out with the compound of the formula (compound A)

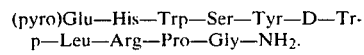

This compound has been obtained according to the method described, for example, in the Swiss Pat. No. 615,662; it has a polypeptide content of about 80% in weight. 1.0 g of copolymer of D,L-lactide and glycolide about 50:50 (average molecular weight of about 53,000) was first dissolved at 25° C. in 50 g of methylene chloride and placed into a reactor provided with a stirring turbine. A solution of 30.4 mg of compound A in 300 micro-l of sterile water was prepared separately, and then this solution was progressively added to the organic mixture. During this addition, the agitation of the mixture was maintained at about 2000 rpm. 30 ml of silicone oil (Dow Corning Fluid 200) were then introduced at 25° C. into the reaction mixture under stirring at the rate of about 2 ml/min. Once the addition of the silicone oil was terminated, the mixture containing the embrionic microcapsules was poured at 15° C. into 2 l of trichlorofluoromethane to permit them to harden, and was stirred for 30 minutes at about 800 rpm. After filtration, the resulting product was dried under reduced pressure until constant weight.

The product thus obtained was isolated with a yield of 70% (of theoretical).

Characterization (a) spherical particles of a diameter comprised between 30 and 40 microns (determined by photographs taken with a scanning electron microscope);

content of coated product 2.07% in weight (efficiency of the encapsulation: 70% of theoretical). The content of coated compound is measured after dissolution of the microcapsules in methylene chloride, extraction with a phosphate buffer (pH 7.4) and titration by using a method by high pressure liquid chromatography.

The microcapsules thus obtained can then be administered in vivo, after, if desired, gamma irradiation (2 Mrad).

EXAMPLE 3

The operations described in Example 2 were repeated, but with a difference that the 30.4 mg of decapeptide were suspended in the methylene chloride without having been dissolved in water beforehand.

EXAMPLE 4

The operations of Example 3 were repeated, but with replacing the trichlorofluoromethane used during the hardening step by a corresponding amount of 1,1,2-trichlorotrifluoroethane. In this case, the operations were carried out at 25° C.

The microcapsules thus obtained were subjected to an ageing test of 12 months: it was thereby found that the kinetics of the decapeptide release in vitro were not modified over this period.

The microcapsules hardened in heptane (reference samples) subjected to the same test showed on the other hand a significant alteration of their properties.

EXAMPLE 5

The following polypeptides were microencapsulated according to the method of Example 3, i.e. without having been dissolved beforehand in water. As in Example 3, the hardening step was carried out at 15° C., and the non-solvent used was trichlorofluoromethane:

(a) Human calcitonine (b) Somatostatine (c) Bovine growth hormone.

The microcapsules obtained are comparable to those obtained with the decapeptide of Example 2 from the point of view of stability and release of the active principle (in vitro and in vivo measurements).

What I claim is:

1. A method of microencapsulation comprising
   (a) dissolving a biocompatible first polymer in a first organic solvent immiscible in water,
   (b) dispersing an aqueous solution of a predetermined medicamentous substance in said first organic solvent,
   (c) introducing a second polymer not compatible with said first polymer into said dispersion at ambient temperature under stirring whereby embrionic microcapsules are caused to form by deposition of said first polymer upon the said dispersed medicamentous substances.
   (d) pouring the mixture obtained in step (c) above into an excess of a second organic solvent not miscible with water and being a non-solvent for said deposited first polymer whereby said microcapsules are hardened by the extraction of said first solvent from the mass of said first polymer deposited upon said medicamentous substance,
   (e) permitting said microcapsules to settle, removing said capsules from said supernatant liquid and drying said capsules,
   characterized therein that the non-solvent utilized in hardening step (d) is a fluorinated or fluorohalogenated aliphatic hydrocarbon, or a mixture of fluorinated or fluorohalogenated hydrocarbons and said fluorinated or fluorohalogenated hydrocarbon or mixture of fluorinated or fluorohalogenated hydrocarbons is used in excess with respect to the sum of the volumes of solvent and non-compatible polymer resulting from phase separation step (c), and said hardening step is carried out at a temperature of from about 0° C. to about 25° C.

2. A method according to claim 1, characterized in that the excess of non-solvent used in the hardening step of the microcapsules is of at least 5:1 with respect to the volume of solvent and non-compatible polymer resulting from the phase-separation step.

3. A method according to claim 1 characterized in that the fluorinated aliphatic hydrocarbon is a fluorohalogenomethane or a fluorohalogenoethane.

4. A method according to one of claims 1 to 3, characterized in that the fluorohalogenated aliphatic hydrocarbon is trichlorofluoromethane, 1,1,2-trichloro-trifluoroethane or 1,2-dichloro-tetrafluoroethane.

5. A method according to claim 1 characterized in that the microcapsules are based on poly-L-lactide, poly-D,L-lactide or a copolymer of D,L-lactide and glycolide.

6. A method according to claim 1 characterized in that the medicamentous water-soluble substance is a polypeptide.

7. A method according to claim 1 characterized in that the medicamentous substance is the release hormone of the luteinizing hormone and of the follicle stimulating hormone (LH—RH), or one of its synthetic analogs, somatostatin or one of its synthetic analogs, human or animal calcitonine, human or animal growth hormone, release hormone of the growth hormone, a cardiopeptide or a natural or a recombined interferon.

8. A method according to claim 7, characterized in that the synthetic analog of LH—RH is chosen among the following polypeptides:

(pyro)Glu—His—Trp—Ser—Tyr—D—Trp—Leu—Arg—Pro—Gly—NH$_2$, (pyro)Glu—His—Trp—Ser—Tyr—D—Phe—Leu—Arg—Pro—Gly—NH$_2$, (pyro)Glu—His—Trp—D—Ser—Tyr—D—Leu—Leu—Arg—Pro—NHR$^1$, or (pyro)Glu—His—Trp—Ser—Tyr—D—Trp—Leu—Arg—Pro—NHR$^1$ (R$^1$=lower alkyl).

9. A method according to claim 1 characterized in that the medicamentous substance is a substance with an anti-inflammatory, antitumorous, immunodepressive, antithrombotic, neuroleptic, antidepressive, antihypertensive effect or a non-toxic water-soluble salt of such a substance.

10. A method of microencapsulation comprising
   (a) dissolving a biocompatible first polymer in a first organic solvent immiscible in water,
   (b) dispersing a methylene chloride suspension of a predetermined medicamentous substance in said first organic solvent,
   (c) introducing a second polymer not compatible with said first polymer into said dispersion at ambient temperature under stirring whereby embrionic microcapsules are caused to form by deposition of said first polymer upon the said dispersed medicamentous substances,
   (d) pouring the mixture obtained in step (c) above into an excess of a second organic solvent not miscible with water and being a non-solvent for said deposited first polymer whereby said microcapsules are hardened by the extraction of said first solvent from the mass of said first polymer deposited upon said medicamentous substance,
   (e) permitting said microcapsules to settle, removing said capsules from said supernatant liquid and drying said capsules,
   characterized therein that the non-solvent utilized in hardening step (d) is a fluorinated or fluorohalogenated aliphatic hydrocarbon, of a mixture of fluorinated or fluorohalogenated hydrocarbons and said fluorinated or fluorohalogenated hydrocarbon or mixture of fluorinated or fluorohalogenated hydrocarbons is used in excess with respect to the sum of the volumes of solvent and non-compatible polymer resulting from phase separation step (c), and said hardening step is carried out at a temperature of from about 0° C. to about 25° C.

* * * * *